United States Patent [19]

Hohenschutz et al.

[11] 4,218,568

[45] Aug. 19, 1980

[54] PREPARATION OF FORMIC ACID

[75] Inventors: Heinz Hohenschutz, Mannheim; Johannes E. Schmidt, Ludwigshafen; Hans Kiefer, Wachenheim, all of Fed. Rep. of Germany

[73] Assignee: BASF Aktiengesellschaft, Fed. Rep. of Germany

[21] Appl. No.: 945,878

[22] Filed: Sep. 26, 1978

[30] Foreign Application Priority Data

Oct. 1, 1977 [DE] Fed. Rep. of Germany ...... 2744313

[51] Int. Cl.$^2$ .............................................. C07C 51/09
[52] U.S. Cl. .................................. 562/609; 568/877
[58] Field of Search ........................ 562/609; 568/877

[56] References Cited

U.S. PATENT DOCUMENTS 3,317,593  5/1967  Enk et al. ............................... 562/609
3,907,884  9/1975  Lynn et al. ............................. 562/609

FOREIGN PATENT DOCUMENTS 1035637  8/1958  Fed. Rep. of Germany .......... 562/609

OTHER PUBLICATIONS

Ullman, 4th Ed., vol. 7, pp. 365-373.

Primary Examiner—Vivian Garner
Attorney, Agent, or Firm—Keil & Witherspoon

[57] ABSTRACT

Formic acid is prepared by hydrolyzing methyl formate, the hydrolysis being carried out in the presence of from 0.5 to 3.0 moles, per mole of methyl formate, of a base which contains tertiary nitrogen atoms, boils at not less than 180° C. under atmospheric pressure and has a pKa from 4 to 9, N-substituted imidazole derivatives being the preferred bases.

2 Claims, No Drawings

PREPARATION OF FORMIC ACID

The present invention relates to a novel process for the preparation of formic acid by hydrolysis of methyl formate.

"Ullmanns Enzyklopädie der technischen Chemie", 4th edition, volume 7, page 365 discloses the preparation of formic acid by acidolysis of formamide with sulfuric acid. However, this process, which is operated on an industrial scale, has the disadvantage that stoichiometric amounts of ammonium sulfate are necessarily produced.

In spite of this disadvantage, the hydrolysis of methyl formate

$$HCOOCH_3 + H_2O \rightleftharpoons HCOOH + CH_3OH$$

which is also known (Ullmann, loc. cit., page 366), and which at first sight appears substantially more advantageous, has not found acceptance in industry, in the main because of the high rate of re-esterification resulting from the strong formic acid acting as a catalyst. It is true that the re-esterification can be substantially repressed by using the special distillation process of German Pat. No. 2,407,157, but this process requires from about 7 to 8 tons of steam per ton of formic acid, so that for this reason alone it is economically virtually ruled out. Furthermore, only the formic acid/water azeotrope is obtained, i.e., an acid of about 75% strength by weight, for which there is little demand, in contrast to the demand for pure or highly concentrated acid.

It is an object of the present invention to provide a more economical method of obtaining formic acid.

We have found that this object is achieved and that formic acid is obtained very advantageously by hydrolysis of methyl formate if the hydrolysis is carried out in the presence of from 0.5 to 3.0 moles, per mole of methyl formate, of a base which contains tertiary nitrogen atoms, boils at not less than 180° C. under atmospheric pressure and has a pKa of from 4 to 9.

Further, it has been found that imidazole derivatives of the general formula I

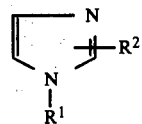

where $R^1$ is a hydrocarbon radical of 1 to 12 carbon atoms and $R^2$ is hydrogen or one of the radicals $R^1$, the number of carbon atoms in $R^1$ and $R^2$ together being from 4 to 12, are particularly suitable for this purpose.

Suitable hydrocarbon radicals in the imidazole derivatives I are, in general, alkyl of 1 to 8 carbon atoms, cyclopentyl, cyclohexyl, phenyl and methylphenyl. Amongst the above, imidazole derivatives where $R^1$ is n-1-alkyl of 4 to 10 carbon atoms and $R^2$ is hydrogen or methyl have proved particularly suitable. Examples of such compounds are 1-(n-1-butyl)-imidazole (pKa 5.9), 1-(n-1-pentyl)-imidazole (pKa 5.9), 1-(n-1-decyl)-imidazole (pKa 5.75), 1-(n-1-butyl)-2-methylimidazole (pKa 7.0) and 1-(n-1-pentyl)-2-methylimidazole (pKa 6.85), and quinoline (pKa 4.7).

For a definition of the pKa values, which are a measure of the base strength, reference may be made, for example, to Landoldt-Börnstein, 6th edition, 7th part, volume II, page 900 et seq. The bases to be used according to the invention are either commercial products or obtainable by conventional methods. Since they are virtually not consumed during the preparation of the formic acid, their price is immaterial.

The advantageous action of the bases is due to the fact that they form a salt-like bond with formic acid. On the one hand, this bond is sufficiently strong to withdraw the formic acid from the hydrolysis equilibrium, whilst on the other hand it is sufficiently weak for the formic acid to be readily distilled again from the base without decomposition and without any significant expenditure of energy.

The molar ratio of methyl formate to monofunctional base—the imidazole derivatives I behave as monofunctional bases, whilst 1,2-diimidazolylethane, for example, behaves as a bifunctional base—is preferably 1:1. However, to complete the hydrolysis it can be advisable to use an excess of base, in particular an excess of from 0.5 to 1 mole, whilst on the other hand a greater excess produces only insignificant advantages. The process can even be carried out economically with less than stoichiometric amounts of the base—in which case part of the formic acid is not bonded—especially if it is not intended to produce anhydrous acid. Because of the presence of the base, an amount of water equimolar with the amount of methyl formate suffices to give satisfactory conversions. Larger amounts of water increase the conversion of methyl formate but entail increased steam consumption in order to concentrate the formic acid solution, as this then becomes necessary.

Since methyl formate boils at 32° C. whilst methanol boils at 65° C. it is not possible to remove the methanol from the hydrolysis equilibrium, during the reaction, by continuous distillation. Hence, the hydrolysis is carried out with a combination of all the components, under a pressure of from 5 to 15 bars and at the corresponding temperatures of from 80° to 150° C., and is taken to a conversion of from about 60 to 95%. The reaction mixture is then let down and advantageously is at the same time directly introduced into a column from which unconverted methyl formate and methanol are taken off at the top, this mixture being separated into its components in the conventional manner in a further column. The bottom products of the first column, namely water, the base and the adduct of formic acid and the base, are next freed from water in a dehydrating column under from 200 to 400 mm Hg, and in a further column the bottom product of the dehydrating column is processed so as to take off the formic acid under from 20 to 100 mm Hg, leaving the base and/or the adduct of formic acid and the base.

Apart from the characteristic of the invention, namely that the hydrolysis is carried out in the presence of the base, all process conditions correspond to conventional techniques or can readily be derived from conventional techniques. This also applies to those measures which are entailed because the base is used. Accordingly, the procedure described above is only one of a plurality of possible embodiments. For example, the process can also be carried out batchwise, using about the same reaction conditions as those mentioned above.

The advantages of the process of the invention are that no by-products which cannot be recycled are obtained, and that with a relatively low energy consumption of from 2 to 3 tons of steam per ton of formic acid pure or highly concentrated aqueous formic acid is obtained directly.

EXAMPLE 1

In a pilot plant, a homogeneous mixture of 2,121 g of 97% strength by weight methyl formate (34.3 moles of methyl formate and 2 moles of methanol), 617 g of water (34.3 moles) and 4,742 g of 1-(1-n-pentyl)-imidazole (34.4 moles) was fed hourly to a tubular reactor of 5 liters capacity. The temperature in the reactor was 130° C. and the pressure was about 10 bars. The material discharged from the reactor per hour comprised 1,001 g (21.75 moles) of formic acid, 753 g (12.55 moles) of methyl formate, 760 g (23.75 moles) of methanol, 226 g (12.55 moles) of water and 4,742 g (34.4 moles) of the base.

The reaction mixture was let down into the middle of a packed column of 8 cm diameter and 150 cm height; from this column, operated with the top at 40° C., and with a reflux ratio of 0.5, a mixture of 760 g of methanol and 753 g of methyl formate was taken off per hour. This mixture was separated in the conventional manner, in a further column, into 752 g of methanol and 746 g of methyl formate The methyl formate was returned to the hydrolysis reactor and the methanol was used for the synthesis of methyl formate, which will not be described in more detail here.

The bottom product, containing the base, from the first column was dehydrated in a packed column (8 cm diameter, 100 cm height, reflux ratio 0.5) under 300 mm Hg. The water (226 g) was also returned to the hydrolysis reactor.

To isolate the formic acid, the bottom product from the dehydrating column was distilled in a packed column (10 cm diameter, 250 cm height, reflux ratio 2, top temperature 35° C.) under 45 mm Hg. Per hour, 991 g of pure formic acid were obtained. This corresponds to a yield of 99%, based on a methyl formate conversion of 64%. The base, which only retained traces of formic acid, was recovered quantitatively and returned to the hydrolysis reactor. The steam consumption for the entire pilot plant was 2.2 tons per ton of pure formic acid.

EXAMPLE 2

A series of experiments was carried out, in each case stirring 1 mole of methyl formate with water and the base in a stirred autoclave at 130° C. under about 10 bars for 5 hours, in order to determine the dependence of the conversion on the type of base used and on the concentrations.

The results are shown in the Table which follows:

| Experiment | Base | Water mole | Base | Conversion % |
|---|---|---|---|---|
| a | 1-(n-1-butyl)-imidazole | 1 | 1 | 76 |
| b | 1-(n-1-butyl(-imidazole | 0.67 | 1 | 82+ |
| c | 1-(n-1-pentyl)-imidazole | 1 | 1 | 66 |
| d | 1-(n-1-pentyl)-imidazole | 2 | 1 | 85 |
| e | 1-(n-1-butyl)-2-methyl-imidazole | 1 | 1 | 75 |
| f | 1-(n-1-pentyl)-2-methyl-imidazole | 1 | 1 | 77 |
| g | 1-(n-1-decyl)-imidazole | 1 | 1 | 64 |
| h | 1.2-di-(1-imidazolyl)-ethane | 1 | 1++ | 64 |
| i | no base, for comparison | 1 | — | 31 |

+ based on water
++ mole equivalents

We claim:

1. A process for the manufacture of formic acid by hydrolyzing methyl formate, wherein the hydrolysis is carried out in the presence of from 0.5 to 3.0 moles, per mole of methyl formate, of a base of the formula I

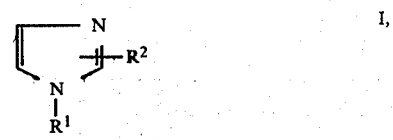

where $R^1$ is a hydrocarbon radical of 1 to 12 carbon atoms and $R^2$ is hydrogen or one of the radicals $R^1$, the number of carbon atoms in $R^1$ and $R^2$ together being from 4 to 12 or 1,2-di(1-imidazoyl)-ethane.

2. A process of claim 1, wherein the base is selected from the group consisting of 1-(n-1-butyl)-imidazole, 1-(n-1-pentyl)-imidazole, 1-(n-1-butyl)-2-methyl-imidazole, 1-(n-1-pentyl)-2-methyl-imidazole, 1-(n-1-decyl)-imidazole and 1,2-di-(1-imidazolyl)-ethane.

* * * * *

UNITED STATES PATENT AND TRADEMARK OFFICE
CERTIFICATE OF CORRECTION

PATENT NO. : 4,218,568

DATED : August 19, 1980

INVENTOR(S) : Heinz Hohenschutz et al

It is certified that error appears in the above—identified patent and that said Letters Patent is hereby corrected as shown below:

In claim 1, line 42, "(1-imidazoyl)" should read --(1-imidazolyl)--.

Signed and Sealed this

Seventeenth Day of February 1981

[SEAL]

Attest:

RENE D. TEGTMEYER

Attesting Officer     Acting Commissioner of Patents and Trademarks